United States Patent [19]
Hange et al.

[11] Patent Number: 5,075,480
[45] Date of Patent: Dec. 24, 1991

[54] PROCESS FOR THE PREPARATION OF VINYLTRICHLOROSILANE

[75] Inventors: Willy Hange, Wittlingen; Claus-Dietrich Seiler, Rheinfelden; Emanuel Fiolitakis, Hennef; Uwe Schön; Helmut Dietsche, both of Rheinfelden, all of Fed. Rep. of Germany

[73] Assignee: Huels Aktiengesellschaft, Marl, Fed. Rep. of Germany

[21] Appl. No.: 693,368

[22] Filed: Apr. 30, 1991

[30] Foreign Application Priority Data

May 18, 1990 [DE] Fed. Rep. of Germany ....... 4016021

[51] Int. Cl.$^5$ ................................................ C07F 7/08
[52] U.S. Cl. ................................................ 556/481
[58] Field of Search ......................................... 556/481

[56] References Cited

U.S. PATENT DOCUMENTS

| 2,770,634 | 11/1956 | Weyenberg | 556/481 |
| 3,560,541 | 2/1971 | Graf et al. | 556/481 |
| 3,666,782 | 5/1972 | Miur et al. | 556/481 |
| 3,706,776 | 12/1972 | Seiler et al. | 556/481 |

FOREIGN PATENT DOCUMENTS 0961499  1/1975  Canada ............................ 556/481

Primary Examiner—Paul F. Shaver
Attorney, Agent, or Firm—Felfe & Lynch

[57] ABSTRACT

The manufacture of vinyltrichlorosilane by reacting vinylchloride with trichlorosilane at a temperature of 400° to 750° C. in a tubular reactor with a rotating displacement body axial-symmetrically disposed therein is improved by heating the reactants to a temperature of 120° to 400° C. prior to their introduction into the reactor.

3 Claims, No Drawings

PROCESS FOR THE PREPARATION OF VINYLTRICHLOROSILANE

FIELD OF THE INVENTION

The present invention relates to a novel process for the continuous preparation of vinyltrichlorosilane from trichlorosilane and vinylchloride by reacting vinylchloride with trichlorosilane at temperatures between 400° and 750° C. and average residence times of 0.2 to 20 seconds at normal pressure in a tubular reactor with a rotating displacement body axial-symmetrically mounted therein.

BACKGROUND OF THE INVENTION

Vinyltrichlorosilane is a useful product which has found its way into a wide field of applications. The esters produced therefrom for example are used for dressing of glass fibers or in the manufacture of cable sheath material.

Copending commonly owned U.S. patent application Ser. No. 642,250, filed Jan. 4, 1991, discloses the principles for the structural design of reactors for the industrial scale production of vinyltrichlorosilane from trichlorosilane and vinylchloride. By using reactors which were manufactured according to the technical data disclosed in said application, it was possible to achieve the reactor output capacities which were proportional to the size of the cross section of the annular reactor ring. Large size reactor units of this type in which the diameter of the outer reactor tube is 60 cm and the length is 250 cm, yield approximately 47 tons of the desired vinyltrichlorosilane per month when they are operated according to the method disclosed in said copending application. An increase in output capacity requires larger reactor diameters and larger reactor cross sections; however, this involves an increased amount of labor and cost.

The possible remedy for the manufacture of larger amounts of vinyltrichlorosilane by providing additional reactor units also has the disadvantage that it involves great expense.

OBJECTS OF THE INVENTION

It is an object of the present invention to provide an improvement in the method of preparing vinyltrichlorosilane described in copending U.S. patent application Ser. No. 642,250, filed Jan. 4, 1991 whereby the space-time yield of the reactor is substantially increased.

Other objects and advantages of the invention will become apparent as the description thereof proceeds.

DESCRIPTION OF THE INVENTION

We have discovered that the above object is achieved by a process for the continuous preparation of vinyltrichlorosilane from vinylchloride and trichlorosilane in tubular reactors with rotating displacement bodies axial-symmetrically disposed therein, wherein the reaction partners are heated to temperatures of 120° to 400° C. prior to being introduced into the reactor.

The use of this process results in an increased space-time yield which is not accompanied by a decrease, in the reaction rates of the reactants to form vinyltrichlorosilane. Indeed, the reaction yield is also improved.

In the context of the present invention, the term "reactants" or "reaction partners" is understood to mean the starting compounds trichlorosilane and vinylchloride. Before their introduction into the reactor, these two compounds must have a minimum temperature of 120° C. in order to improve the space-time yield of the method described in said copending application. The increases in space-time yield are particularly great when these compounds have a temperature of 140° to 280° C. when they are introduced into the reactor.

The individual reactants may be heated individually. After such separate preheating, the compounds are mixed—preferably without heat loss—and, as a mixture, introduced into the reactor. This is the preferred method of operation.

It is, however, also possible to pre-mix the reactants, preheat this mixture to temperatures up to 400° C., and then introduce it into the reactor.

It is essential that the reactants, upon introduction into the reactor, exhibit temperatures in the range of 120° to 400° C. Hence, care must be taken that there is no significant temperature drop after the reactants have been heated. Those skilled in the art know what means are available to avoid such a temperature drop.

When checking the temperature of the heated reactants, care must be taken that the gas temperature of the compounds is measured and not the temperature of the medium which is used to heat the reactants. After the introduction of the reactants into the reactor, the process is carried out as described in copending patent application Ser. No. 642,250.

The following examples illustrate the present invention and will enable others skilled in the art to understand it more completely. It should be understood, however, that the invention is not limited solely to the particular examples given below.

EXAMPLES 1 TO 7

A mixture of vinylchloride and trichlorosilane in a mol ratio of 1:1.4 was introduced into a reactor 250 cm in length and having an internal diameter of 60 cm wherein a rotating displacement body of the same length and 56 cm in diameter was axial-symmetrically mounted therein. Prior to being introduced into the reactor, both the vinylchloride and the trichlorosilane were individually heated to the temperatures shown in Table 1 below and were then admixed and introduced into the reactor. In all examples, the interior temperature of the reactor ranged between 600° and 640° C. The residence times ranged between 1.0 and 1.8 seconds. The speed of rotation of the displacement body was constant at 50 revolutions per minute. After its discharge from the reactor, the reaction mixture was condensed and then worked up by means of distillation.

TABLE 1

| | Example | | | | | | |
|---|---|---|---|---|---|---|---|
| | 1 (comparison) | 2 (comp.) | 3 | 4 | 5 | 6 | 7 |
| Introduction temperature of reactants (°C.) | 50 | 100 | 120 | 140 | 140 | 280 | 400 |
| Yields of vinyltrichlorosilane (tons/month) | 47 | 55 | 65 | 85 | 105 | 130 | 145 |
| Yield of vinyl- | 70 | 70 | 72 | 73 | 74.5 | 76 | 77 |

TABLE 1-continued

|  | Example | | | | | |
|---|---|---|---|---|---|---|
|  | 1 (comparison) | 2 (comp.) | 3 | 4 | 5 | 6 | 7 |
| trichlorosilane (%) (ref. to vinylchloride reacted) | | | | | | | |

The use of the method of operation in accordance with the instant invention results in a considerable increase in the capacity of a given reactor. Also, the conversion of the introduced vinylchloride into vinyltrichlorosilane can be improved.

Whereas preheating of the reactants to a temperature range between 50° and 120° C. increases the reactor capacity only to a limited extent, there is a strong increase in reactor capacity in a temperature range between 120° and 280° C. obtained by the introduction of a corresponding preheated reactant mixture. The reactor capacity can be doubled by increasing the intake temperature of the reactants into the reactor system from 120° to 280° C. Heating of the reactants prior to their introduction into the reactor to temperatures between 280° and 400° C. further increases the capacity of the reactor.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. In a process for the continuous manufacture of vinyltrichlorosilane by reacting vinylchloride with trichlorosilane at a temperature of 400° to 750° C. and average residence times of 0.2 to 20 seconds at normal pressure in a tubular reactor with a rotating displacement body axial-symmetrically disposed therein, the improvement which comprises heating the reactants to temperature of 120° to 400° C. prior to their introduction into the reactor.

2. The process of claim 1, wherein the reactants are heated to a temperature of 140° to 280° C.

3. The process of claim 1, wherein the reactants are heated separately and are then admixed and subsequently introduced into the reactor.

* * * * *